(12) United States Patent
Nickel et al.

(10) Patent No.: US 9,404,842 B2
(45) Date of Patent: Aug. 2, 2016

(54) METHODOLOGY AND APPARATUS FOR TESTING CONDUCTIVE ADHESIVE WITHIN ANTENNA ASSEMBLY

(71) Applicant: Apple Inc., Cupertino, CA (US)

(72) Inventors: Joshua G. Nickel, San Jose, CA (US); Chun-Lung Chen, Sunnyvale, CA (US); Tseng-Mau Yang, Kitchener (CA); Nicholas G. Merz, San Francisco, CA (US); Robert W. Schlub, Cupertino, CA (US); Boon W. Shiu, San Jose, CA (US); Erica J. Tong, Pacifica, CA (US)

(73) Assignee: Apple Inc., Cupertino, CA (US)

( * ) Notice: Subject to any disclaimer, the term of this patent is extended or adjusted under 35 U.S.C. 154(b) by 337 days.

(21) Appl. No.: 13/968,166

(22) Filed: Aug. 15, 2013

(65) Prior Publication Data

US 2015/0050893 A1    Feb. 19, 2015

(51) Int. Cl.
*G01N 19/04* (2006.01)
*G01N 3/56* (2006.01)
*H04B 17/00* (2015.01)
*G01N 3/08* (2006.01)
*G01N 3/24* (2006.01)
*H04B 17/16* (2015.01)

(52) U.S. Cl.
CPC .. *G01N 3/56* (2013.01); *G01N 3/08* (2013.01); *G01N 3/24* (2013.01); *G01N 19/04* (2013.01); *H04B 17/00* (2013.01); *H04B 17/16* (2015.01)

(58) Field of Classification Search
CPC ............ G01N 19/04; G01N 3/00; G01N 3/08
USPC .............. 73/150 A, 827, 818, 788; 455/67.14
See application file for complete search history.

(56) References Cited

U.S. PATENT DOCUMENTS

| | | | | |
|---|---|---|---|---|
| 4,843,313 A | * | 6/1989 | Walton ................. | G01R 1/0433 324/757.04 |
| 5,861,759 A | * | 1/1999 | Bialobrodski ........... | G01R 3/00 324/750.23 |
| 6,260,415 B1 | * | 7/2001 | Goebel .................... | G01D 5/48 73/582 |
| 6,559,666 B2 | * | 5/2003 | Bernier ............... | G01R 31/2886 324/750.16 |
| 6,853,087 B2 | * | 2/2005 | Neuhaus ................. | H05K 3/325 257/700 |
| 7,034,403 B2 | * | 4/2006 | Divigalpitiya .......... | H01L 24/29 257/782 |
| 7,567,883 B2 | * | 7/2009 | Heaton ............ | G01R 31/31725 324/76.23 |

(Continued)

OTHER PUBLICATIONS

Nath et al., U.S. Appl. No. 13/487,149, filed Jun. 1, 2012.

*Primary Examiner* — Lisa Caputo
*Assistant Examiner* — Nigel Plumb
(74) *Attorney, Agent, or Firm* — Treyz Law Group, P.C.; Michael H. Lyons (57) ABSTRACT

Damage to conductive material that serves as bridging connections between conductive structures within an electronic device may result in deficiencies in radio-frequency (RF) and other wireless communications. A test system for testing device structures under test is provided. Device structures under test may include substrates and a conductive material between the substrates. The test system may include a test fixture for increasing tensile or compressive stress on the device structures under test to evaluate the resilience of the conductive material. The test system may also include a test unit for transmitting RF test signals and receiving test data from the device structures under test. The received test data may include scattered parameter measurements from the device structures under test that may be used to determine if the device structures under test meet desired RF performance criteria.

14 Claims, 9 Drawing Sheets

(56) References Cited

U.S. PATENT DOCUMENTS

| | | | | |
|---|---|---|---|---|
| 7,746,053 B2* | 6/2010 | Ribeiro | | G01R 31/303 324/756.01 |
| 7,906,982 B1* | 3/2011 | Meade | | G01R 31/318511 324/754.01 |
| 2002/0057098 A1* | 5/2002 | Aldaz | | G01R 1/07342 324/750.16 |
| 2007/0099447 A1* | 5/2007 | Hayashi | | G01R 31/2893 439/73 |
| 2011/0277556 A1* | 11/2011 | Peecock | | G01L 5/0033 73/827 |
| 2011/0291679 A1* | 12/2011 | Pagani | | G01R 31/3172 324/750.01 |
| 2012/0013348 A1* | 1/2012 | Chen | | G01R 1/0408 324/555 |
| 2012/0178386 A1* | 7/2012 | Pascolini | | H04B 1/525 455/84 |
| 2013/0068034 A1* | 3/2013 | Takashima | | G01N 3/068 73/800 |
| 2013/0082895 A1* | 4/2013 | Shiu | | C25D 7/00 343/866 |
| 2013/0106455 A1* | 5/2013 | Edwards | | G01R 31/2891 324/754.1 |
| 2013/0199285 A1* | 8/2013 | Murtonen | | G01N 19/04 73/150 R |
| 2013/0321012 A1* | 12/2013 | Nath | | G01R 31/2808 324/750.02 |

* cited by examiner

METHODOLOGY AND APPARATUS FOR TESTING CONDUCTIVE ADHESIVE WITHIN ANTENNA ASSEMBLY

BACKGROUND

This relates generally to wireless communications circuitry, and more particularly, to electronic devices having wireless communications circuitry.

Electronic devices such as portable computers and cellular telephones are often provided with wireless communications capabilities. For example, electronic devices may use communications circuitry such as cellular telephone circuitry, wireless local area network communications circuitry, satellite navigation system receivers, and other antenna systems. Integration of increasingly complex antenna systems into electronic devices requires the materials that join separate structural modules in the circuitry to have particular properties, such as characteristics that establish and maintain conductivity between separate structural modules when under a specified amount of tension.

It may therefore be desired to have improved methods and systems for testing materials that are used to join structures in an electronic device for desired performance qualities.

SUMMARY

A test system for characterizing device structures under test may be provided. The test system may include a test unit and a test fixture. The device structures under test may include a conductive material, which may be an adhesive material. The adhesive material may be a pressure-sensitive adhesive. The test fixture may receive the device structures under test. The test fixture may activate the adhesive material in the device structures under test by applying pressure to it while the device structures under test are received in the test fixture. Activating the adhesive material may include applying compressive stress to the device structures under test.

The test fixture may apply stress to the device structures under test once the adhesive material has been activated. The type of stress applied to the device structures under test is different than the type of stress applied to activate the adhesive material. The test fixture may apply tensile stress to the device structures. Different amounts of stress may be applied to the device structures under test during testing. The applied tensile stress on device structures under test may be increased at regular increments.

While tensile stress is applied to the device structures under test, the test unit may gather test data on the device structures under test. The test unit may include a radio-frequency tester operable to gather scattering parameter measurements on the device structures under test. The gathered test data may include reflection coefficient measurements and multiport scattering parameter measurements on the device structures under test. The gathered test data may be analyzed to determine whether the conductive material (e.g. adhesive material) satisfies design criteria.

The test system may include a test probe that receives radio-frequency test signals from the test unit. The test probe may be coupled to the device structures under test. The test probe may include a signal conductor and a ground conductor. The device structures under test may be interposed between the signal conductor and the ground conductor while the device structures under test are received within the test fixture.

The test system may also have a radio-frequency cable that has a first end coupled to the test unit and a second end mated to a corresponding coaxial cable in the device structures under test via a radio-frequency coaxial test connector.

Further features of the present invention, its nature, and various advantages will be more apparent from the accompanying drawings and the following detailed description.

DETAILED DESCRIPTION

An electronic device may contain antenna structures or systems that include separate components. Conductive materials may be required to establish conductivity between separate components in the antenna system to maintain functionality of the communication circuitry. It may be desirable to test individual components in the electronic device prior to actually assembling the components within the device. Testing parts prior to assembly can help identify (at an early stage) potentially problematic issues that can negatively affect the performance of device 10 during normal user operation. For example, it may be desirable to characterize structures associated with antennas, because the integrity of these structures can often impact the antenna/wireless performance of device 10. Such types of structures that can potentially impact the radio-frequency (RF) performance of device 10 are sometimes referred to as device structures under test (DSUTs). A test system such as test system 100 of FIG. 1 may be used for testing the RF characteristics of device structures under test such as DSUTs 10. DSUTs 10 may be any structures within an electronic device that needs to be tested for functionality in accordance with desired performance standards.

Examples of DSUTs 10 that may be characterized prior to being assembled within the electronic device include conductive housing structures (e.g., conductive housing structures that form part of antennas), antenna feed structures (e.g., flexible antenna circuits, shorting pins, radio-frequency cables, etc.), radio-frequency gain altering circuits such as power amplifiers and low noise amplifiers, matching circuits, filters, and other structural components of antenna structures. DSUTs 10 may include portions of antenna structures such as inverted-F antenna structures, planar inverted-F antenna structures, loop antennas, dipoles, monopoles, open and closed slot antennas, hybrid designs that include more than one antenna structure of these types, or other suitable antenna structures. Portions of DSUTs 10 may include conductive material such as conductive adhesives, foams, tapes, pressure sensitive adhesives, conductive gaskets, conductive fabric foams, ultraviolet-activated adhesives, and thermal-activated adhesives.

Figure 1:
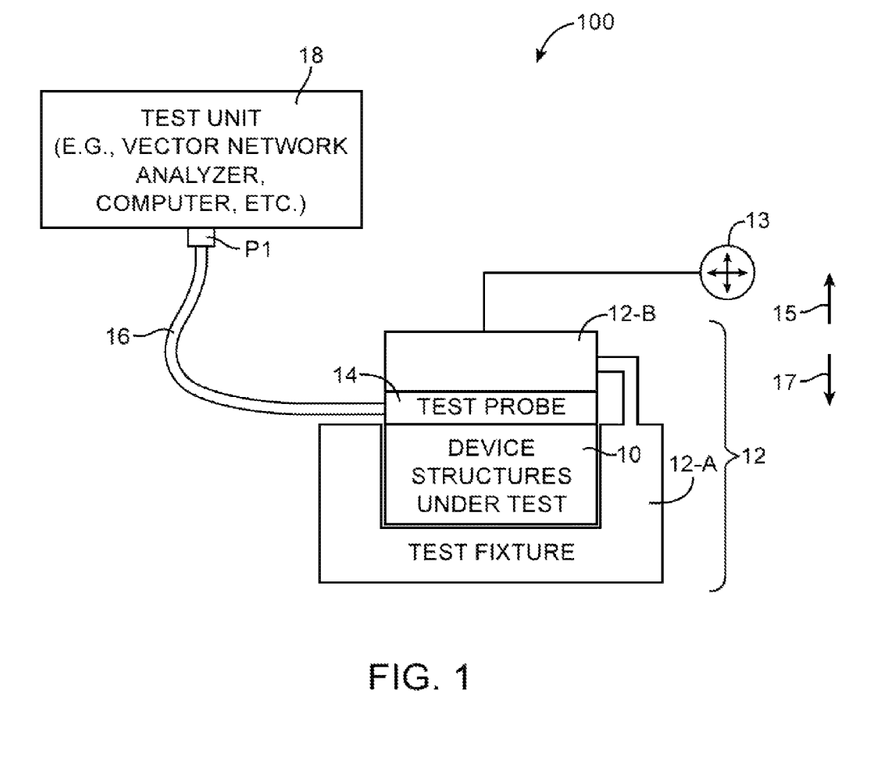
FIG. 1 is a schematic diagram of an illustrative test system for testing device structures in an electronic device in accordance with an embodiment of the present invention.

DSUTs 10 may be placed within a test fixture such as test fixture 12 of test system 100. Test fixture 12 may include a bottom portion 12-A which receives DSUTs 10, and a top portion 12-B. Portions 12-A and 12-B may both be part of the same test fixture 12. Top portion 12-B may be adjustable in multiple directions using positioner 13. For example, top portion 12-B may be configured to move in vertical directions 15 and 17. Top portion 12-B may be configured to exert a desired amount of force on DSUTs 10 during test operations.

A test probe such as test probe 14 may contact DSUTs 10. Test probe 14 may include signal and ground conductors that are electrically connected to device structures under test in the mated position (i.e., the signal and ground conductors of test probe 14 may be electrically coupled to DSUTs 10 while test probe 14 is mated with DSUTs 10). The positioning of test probe 14 in FIG. 1 between the bottom surface of top portion 12-B of test fixture 12 and the upper region of DSUTs 10 is merely exemplary. In general, test probe 14 may be placed anywhere in the vicinity of DSUTs 10 in a way that enables test data to be gathered successfully. For example, test probe 14 may measure RF characteristics of DSUTs 10 when top portion 12-B exerts a tensile force on device structures 10. As another example, test probe 14 may gather test data from DSUTs 10 when top portion 12-B is used to apply compressive force on device structures under test 10.

Test probe 14 may relay gathered test data through a cable such as cable 16 to a test unit such as test unit 18. Test unit 18 may be any processing unit or analyzer that receives and analyzes the gathered test data from test probe 14 to determine whether the RF characteristics of DSUTs 10 meet performance criteria. Test unit 18 may be a computer, a vector network analyzer, a spectrum analyzer, a signal generator, and/or other radio-frequency test equipment suitable for transmitting/receiving radio-frequency test signals and obtaining/storing radio-frequency test measurements. Test unit 18 may include a radio-frequency tester used to generate RF test signals that are fed to DSUTs 10 via cable 16 to the signal conductor of test probe 14. Test unit 18 may have port P1 to which a cable such as cable 16 is connected. Cable 16 may have a first end that is connected to port P1 and a second end connected to test probe 14. Connected using this arrangement, test unit 18 may be configured to gather desired radio-frequency measurements such as radio-frequency metrics from DSUTs 10.

Even without being connected to other components to form a completed antenna assembly, DSUTs 10 may emit radio-frequency signals when being energized by the test signals generated using test unit 18. As electromagnetic test signals are transmitted by test unit 18 and applied to DSUTs 10 through cable 16 and test probe 14, test unit 18 may receive reflected signals via cable 16 and test probe 14 (i.e., signals that were reflected from DSUTs 10 in response to the transmitted RF test signals). The reflected signals gathered in this way may be used to compute a reflection coefficient (sometimes referred to as an input reflection scattering parameter or S11 measurement).

Test unit 18 may have any number of ports and any number of cables connected to the ports to gather desired measurements. For example, test unit 18 may have n number of ports and n number of cables, each connected to test unit 18 and DSUTs 10. Test unit 18 may compute reflection coefficients for test data received via each cable and port (e.g., S22, S33 ... Snn parameter or an Snn scattering parameter). Test unit 18 may also compute forward transfer coefficients (sometimes referred to as a forward transfer scattering parameter or S21 measurements) for any combination of test data received from the ports and cables (e.g., S12, S21, S23, S32, S13, S31, etc.). An example of obtaining multiport scattering parameter measurements is described in more detail later in connection with FIGS. 7 and 8.

Test unit 18 may, for example, analyze the scattering parameter test data to determine whether DSUTs 10 satisfy design criteria. If the gathered test data deviates from predetermined levels by an unacceptable amount, DSUTs 10 may be marked as defective. If the gathered test data deviates from the predetermined level by a tolerable amount, DSUTs 10 may be marked as a passing device. The use of test unit 18 for obtaining scattering parameter test data from DUT 10 is merely illustrative and does not serve to limit the scope of the present invention. If desired, test unit 18 may be used to gather other types of radio-frequency measurements from DSUTs 10.

Figure 2:
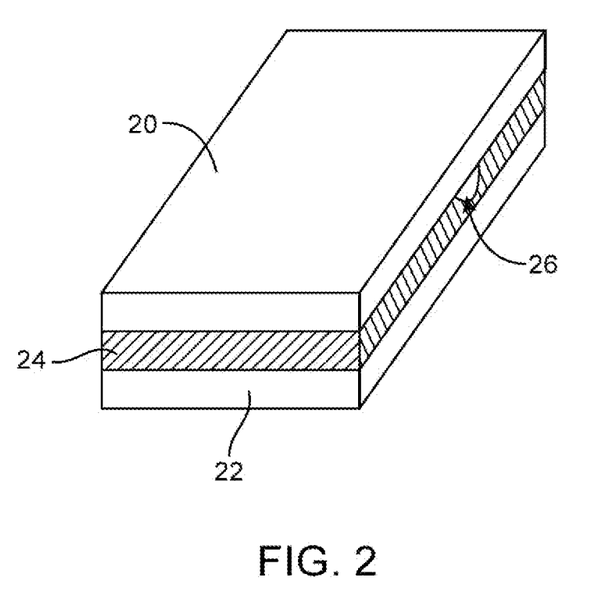
FIG. 2 is a diagram of device structures under test in accordance with an embodiment of the present invention.

In some embodiments of the present invention, as shown in FIG. 2, DSUTs 10 may include a top substrate such as top substrate 20, a bottom substrate such as bottom substrate 22, and conductive material such as conductive material 24 for bonding top substrate 20 and bottom substrate 22 together (e.g., conductive material 24 may be interposed between top substrate 20 and bottom substrate 22). Top substrate 20, conductive material 24, and bottom substrate 22 may be arranged in a stack formation. DSUTs 10 (sometimes also referred to as stack under test 10) may be part of an antenna structure for an electronic device.

Substrates 20 and 22 may be, for example, flexible or rigid printed circuit boards. Substrates 20 and 22 may be flexible printed circuit boards, rigid printed circuit boards, rigid-flex circuits, or other suitable types of circuit boards. Substrates 20 and 22 may be formed from any suitable material, including conductive materials such as aluminum, steel, copper, and brass. Conductive material 24 may be any material that serves as a conductive mechanism between the top and bottom substrates. Conductive material 24 may be conductive adhesives, foams, tapes, pressure sensitive adhesives, conductive gaskets, conductive fabric foams, ultraviolet-activated adhesives, thermal-activated adhesives, a combination of these materials, and/or other types of conductive materials. Different types of conductive material may require different methods of activation and/or curing for maintaining conductivity between substrates 20 and 22 (e.g., pressure sensitive adhesives may be activated via mechanical pressure, thermal-activated adhesives may be activated via heat, etc.).

When an electronic device is in a stressed environment, the electronic device may be vulnerable to various deficiencies in wireless communications due to damage incurred in structures within the electronic device. For example, when an electronic device is dropped or is handled roughly in a way that places stress on structures within the device, conductive material that serves as bridging connections between conductive structures within the device, such as adhesive joining two flexible circuit boards in an antenna structure, may tear or crack. As shown in FIG. 2, when stack under test 10 is placed under stress, breaks or tears such as tear 26 may occur in conductive material 24.

Figure 3A:
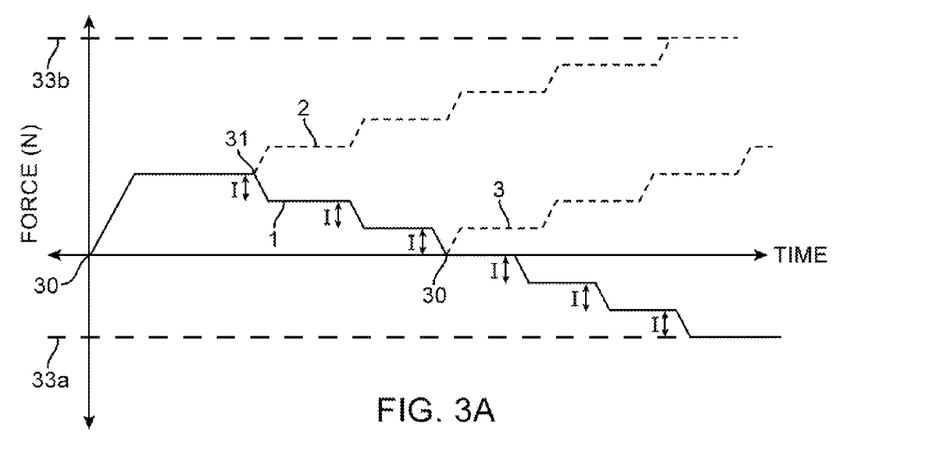
FIG. 3A is a plot showing how force may be applied to the device structures under test in accordance with an embodiment of the present invention.
Figure 3B:
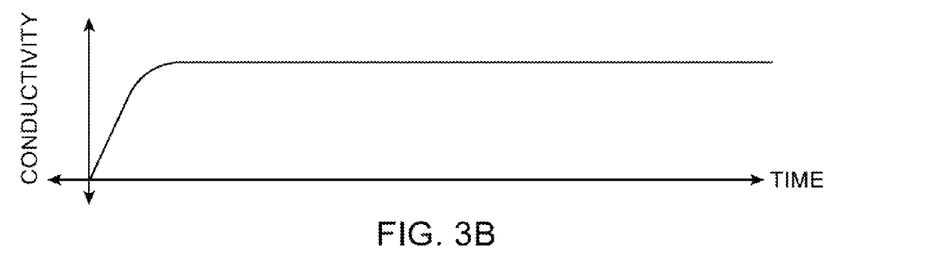
FIGS. 3B and 3C are plots showing the conductivity of different device structures under test while force is applied to the device structures as shown in FIG. 3A in accordance with an embodiment of the present invention.
Figure 3C:
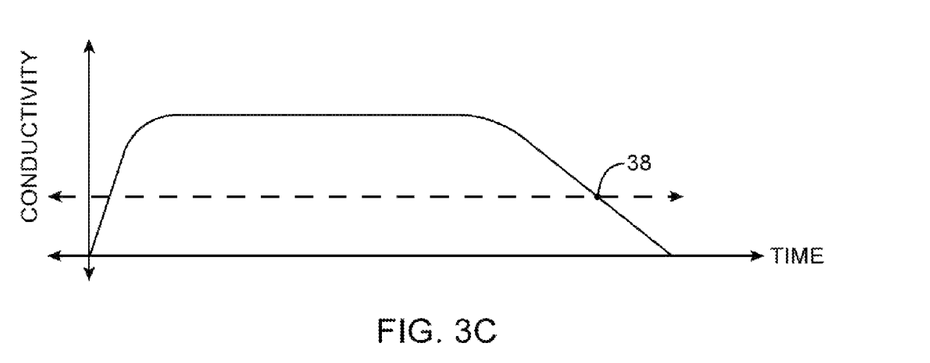

FIG. 3A shows a plot of force while DSUTs 10 are being tested in test fixture 12 of FIG. 1. "Positive" force as shown in FIGS. 3A-3C indicates a force experienced by the device structures under test that compresses device structures under test 10, whereas a "negative" force indicates a force experienced by the device structures under test that stretches the device structures under test. A decrease in force indicates that a force is exerted in a direction that will eventually apply tensile stress to DSUTs 10a. DSUTs 10 may be a stack under test as shown in FIG. 2 or other structures under test.

Test fixture 12 may initially be set to a neutral or equilibrium point 30, where top portion 12-A of the test fixture is in contact with test probe 14 while exerting a negligible amount of force on DSUTs 10. Test fixture 12 may then increase the amount of force on device structures under test such that DSUTs 10 experiences a compressive force. Test fixture 12 may exert this compressive force by moving the top portion 12-B in a downward direction toward DSUTs 10.

Conductive material 24 in DSUTs 10 as shown in FIG. 2 may be a pressure-activated adhesive (PSA). Conductive material 24, sometimes referred to as PSA 24, may not initially form a secure bond between substrates 20 and 22 when it is placed between the two substrates. PSA 24 may require the application of pressure in order to activate molecular interactions that allow PSA 24 to securely adhere to substrates 20 and 22 and consequently, to form a bond between the substrates in DSUTs 10. PSA 24 may be activated when DSUTs 10 experience a certain amount of compressive force after a certain amount of time at activation point 31. Once PSA 24 is activated, test fixture 12 may reduce the compressive force on DSUTs 10 in regular step-wise increments I (i.e., apply force in the opposite direction) as shown by line 1 of FIG. 3A until the force experienced by DSUTs 10 settles back to equilibrium point 30, where the top portion 12-B of the test fixture just contacts the DSUTs without placing the device structures under any significant amount of stress (compressive or tensile).

Test fixture 12 may then exert tensile stress on DSUTs 10 (a "negative" force on FIG. 3A) as shown by line 1. Test fixture 12 may exert this tensile force by moving the top portion 12-B in an upward direction away from DSUTs 10 while DSUTs 10 is still connected to top portion 12-B of the test fixture. The tensile stress applied may be regularly increased in steps (i.e. increments I) until a maximum predetermined amount of tensile stress 33a.

When a predetermined amount of tensile stress 33a is reached, text fixture portion 12-B may stop moving in a direction away from DSUTs 10 and therefore stop exerting tensile stress on DSUTs 10. Test fixture portion 12-B may be gently lowered to a point such as equilibrium point 30 where no compressive or tensile force is exerted on DSUTs 10. DSUTs 10 may then be removed from test fixture 12 so that another device structure under test may be placed in test fixture 12 for testing.

Because compressive stress may also result in damage or deterioration of PSA 24, DSUTs 10 may also be tested for resilience against compressive stress after PSA 24 is activated. For example, instead of reducing compressive pressure on DSUTs 10 after activation point 31, test fixture 12 may continue to increase compressive force on DSUTs 10 in regular increments until reaching a maximum predetermined amount of compressive stress 33b, as shown by line 2 of FIG. 3A. As another example, test fixture 12 may first reduce the compressive force after activation point 31 until equilibrium point 30 (as in FIG. 3A) and then apply compressive force on DSUTs 10 in regular increments as shown by line 3 of FIG. 3A until a predetermined amount of compressive stress.

FIGS. 3B and 3C show plots of variation in conductive properties of two different examples of DSUTs 10 while force is applied to DSUTs 10 in accordance with the plot shown in FIG. 3A. FIG. 3B shows an exemplary graph of the conductivity of DSUTs 10 that include a conductive material 24 (e.g., a pressure sensitive adhesive) that is resilient to the stress (e.g. compressive and/or tensile) administered to DSUTs 10 during testing. The resilience of conductive material 24 under stress may affect the ability of DSUTs 10 to successfully receive and transmit electrical signals between substrates 20 and 22 (i.e., the conductivity of DSUTs 10). Therefore, the resilience of conductive material 24 and the conductivity of DSUTs 10 may affect RF measurements such as scattering parameters (e.g. S11, S12, etc.) gathered in response to transmitting a RF test signal to DSUTs 10.

Conductive material 24 may be able to withstand a substantial amount of tensile stress. For example, conductive material 24 may be able to maintain its integrity under a predetermined amount of tensile stress 33a applied during testing to DSUTs 10. As a result of the strength of conductive material 24, DSUTs 10 may be able to maintain conductivity under the stress administered during testing and produce desirable test data (e.g., scattering parameters such as S11).

Similarly, conductive material 24 may be able to withstand a substantial amount of compressive stress. For example, conductive material 24 may be able to maintain its integrity under a predetermined amount of compressive stress 33b applied during testing to DSUTs 10. As a result of the strength of conductive material 24, DSUTs 10 may be able to maintain conductivity under the stress administered during testing and produce desirable test data (e.g., scattering parameters such as S11).

In contrast to FIG. 3B, FIG. 3C shows an exemplary graph of the conductivity of DSUTs 10 that include a conductive material 24 (e.g., a pressure sensitive adhesive) that deteriorates under the stress (e.g. compressive and/or tensile) administered to DSUTs 10 during testing. Conductive material 24 may be able to withstand a certain amount of stress but begin to lose its integrity after too much stress is applied. For example, conductive material 24 may maintain its integrity under multiple step-wise increases of stress, but begin to deteriorate under the amount of stress applied during a particular test point such as test point 38. Conductive material 24 may be a material that is prone to breakage or tearing when a certain amount of compressive or tensile stress is applied, resulting in breaks or tears such as tear 26 as shown in FIG. 2. Deterioration or tears 26 in conductive material 24 may cause the conductivity of DSUTs 10 to affect its RF capabilities, resulting in undesirable test data such as scattering parameters (e.g., S11).

Figure 4A:
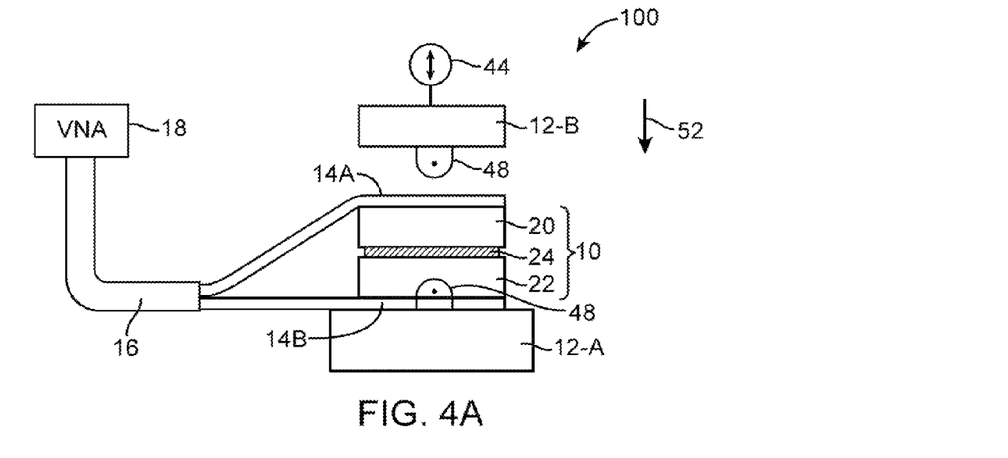
FIGS. 4A, 4B, and 4C are diagrams of a test system for exerting different types of forces on device structures under test in accordance with an embodiment of the present invention.
Figure 4B:
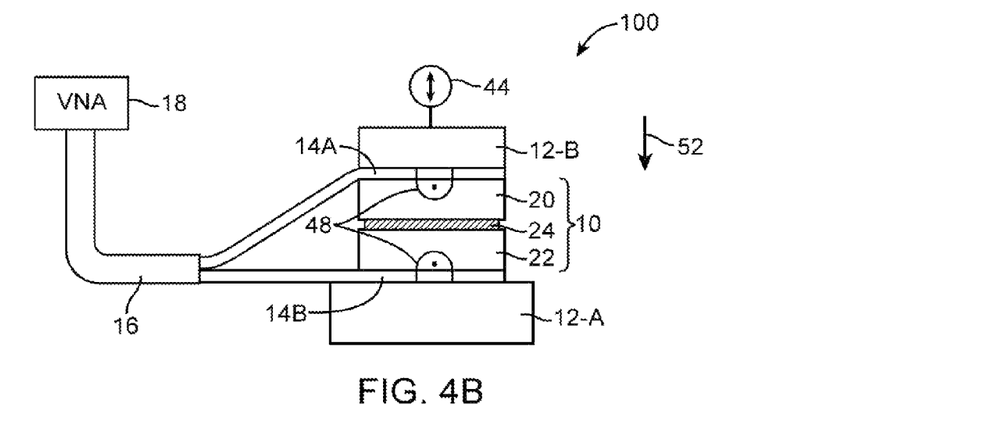
Figure 4C:
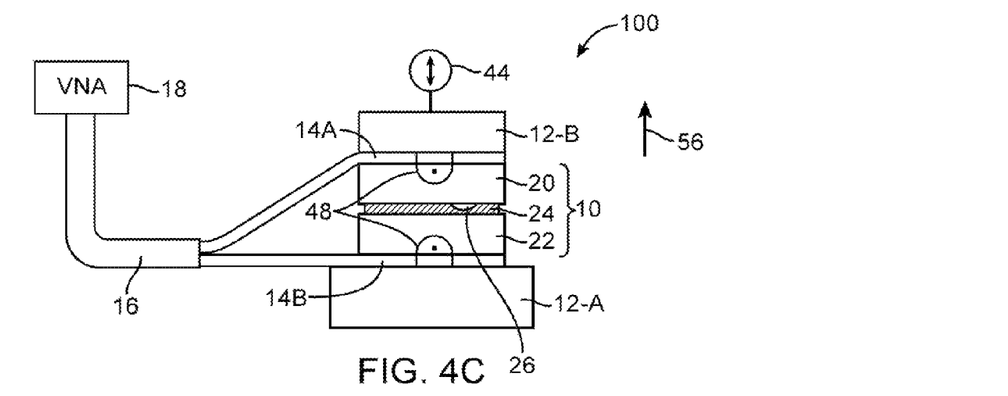

FIGS. 4A-4C show test system 100 exerting different types of forces on DSUTs 10. DSUTs 10 may be a stack under test as shown in FIG. 2 or other structures under test. FIG. 4A shows a test system with vector network analyzer (VNA) 18 connected to test fixture 12 via coaxial cable 16. Device structures under test 10 may rest on bottom portion 12-A of the test fixture. Test probe 14 may be formed from a signal trace 14-A and ground trace 14-B. Signal trace 14-A and ground trace 14-B may be made of conductive sheets of metal. Signal trace 14-A may be positioned on the top surface of DSUTs 10 such as on the top surface of top substrate 20. Ground trace 14-B may be positioned between bottom substrate 22 of device structures under test 10 and test fixture portion 12-A. The positioning of signal trace 14-A and ground trace 14-B is merely exemplary; signal traces and ground traces may be placed in any number of positions contacting DSUTs 10 such that the signal trace may successfully transmit test RF signals and gather RF test data from DSUTs 10.

Test probe 14 may transmit test signals and gather test data relating to RF characteristics of DSUTs 10 during testing. VNA 18 may receive test data such as S11 parameter test data from DSUTs 10 via test probe 14 and cable 16. To secure device structures 10 to the test fixture, securing structures such as clamps 48 may be implemented to fix or clamp portions of DSUTs 10 to the test fixture. For example, at the beginning of testing, bottom substrate 22 may be connected to bottom portion 12-A of the test fixture using clamp 48. This is merely an example; device structures under test 10 may be secured to the test fixture using any number or types of fastener or attaching mechanism.

Upper portion 12-B of the test fixture may be moved in a vertical direction by positioner 44. At the beginning of testing, upper portion 12-B may be in a position above DSUTs 10 that does not contact test probe 14-A or DSUTs 10. Upper portion 12-B of the test fixture may be detached or part of the same test fixture as bottom portion 12-B. Upper portion 12-B of the test fixture may be connected to bottom portion 12-A of the test fixture by additional test fixture structures. Upper portion 12-B may be moved in downward direction 52 toward test probe 14-A and DSUTs 10.

FIG. 4B shows the test system applying force to DSUTs 10. Upper portion 12-B of test fixture 12 may be moved vertically in a downward direction 52 using positioner 44 until test fixture 12-B contacts test probe 14-A. Upper portion 12-B of the test fixture may be attached to top substrate 20 using an additional clamp 48. Clamp 48 may be used to secure top substrate 20 to test fixture 12-B. Test fixture 12-B may continue to move in downward direction 52 even after it has contacted test probe 14-A to compress device structures under test 10. Conductive material 24 may be a pressure-sensitive adhesive and compression of device structures 10 may activate conductive material 24. Activating conductive material 24 may allow top substrate 20 and bottom substrate 22 of the device structures to be securely bonded to each other so that DSUTs 10 may maintain conductivity in stressed environments.

Test fixture 12-B may continue moving in a downward direction 52 after activation of conductive material 24 to administer more compressive stress on DSUTs 10 as illustrated by line 2 of FIG. 3A. Alternatively, test fixture 12-B may move in an upward direction to reduce compressive stress on DSUTs 10 to an equilibrium point before applying more compressive stress to DSUTs 10 as illustrated by line 3 of FIG. 3A. Compressive stress may cause deterioration of conductive material 24. The integrity of conductive material 24 may affect the conductivity of DSUTs 10 and consequently affect S11 scattering parameter test data collected from DSUTs 10 via cable 16. Deterioration of conductive material 24 may cause S11 parameter test data of DSUTs 10 to deviate from desired performance data.

However, if conductive material 24 is formed from a material resilient to compressive stress, DSUTs 10 may maintain conductivity under a particular level of compressive stress. For example, conductive material 24 may not deteriorate when DSUTs 10 experience a predetermined level of compressive stress $33b$ administered during testing. This may result in desirable S11 parameter test data and/or other satisfactory RF performance criteria and allow DSUTs 10 to pass on to subsequent testing or be used in a product device.

Test fixture 12-B may stop moving in downward direction 52 once conductive material 24 is activated to bond the top and bottom substrates in DSUTs 10 and once test fixture 12-B is securely fastened to top substrate 20 with a clamp such as clamp 48. After compression of DSUTs 10, test fixture 12-B may then begin to move in an upward vertical direction 56 using positioner 44, as shown in FIG. 4C. Because top substrate 20 is connected to upper portion 12-B of the test fixture and bottom substrate 22 is connected to bottom portion 12-A of the test fixture, DSUTs 10 may experience tensile stress. Conductive material 24 may be stretched as the top substrate 20 is slowly pulled away from bottom substrate 22.

Tensile stress may cause breaks or tears in conductive material 24 such as tear 26 as shown in FIG. 4C. The integrity of conductive material 24 may affect the conductivity of DSUTs 10 and consequently affect S11 scattering parameter test data collected from DSUTs 10 via cable 16. Tear 26 may cause S11 parameter test data of DSUTs 10 to deviate from desired performance data.

However, if conductive material 24 is formed from a material resilient to tensile stress, DSUTs 10 may maintain conductivity under particular level of tensile stress. For example, conductive material 24 may not deteriorate and create tear 26 when DSUTs 10 experience a predetermined level $33a$ of tensile stress administered during testing. This may result in desirable S11 parameter test data and/or other satisfactory RF performance criteria and allow DSUTs 10 to pass on to subsequent testing or be used in a product device.

This configuration of test system 100 is merely exemplary. Test system 100 may be configured to apply any number and type of additional stressors such as shock and vibrations to DSUTs 10 using test fixture 12 or any suitable test fixture. Test system 100 may also be configured to test DSUTs 10 after exposure to environmental or reliability testing conditions.

Figure 5:
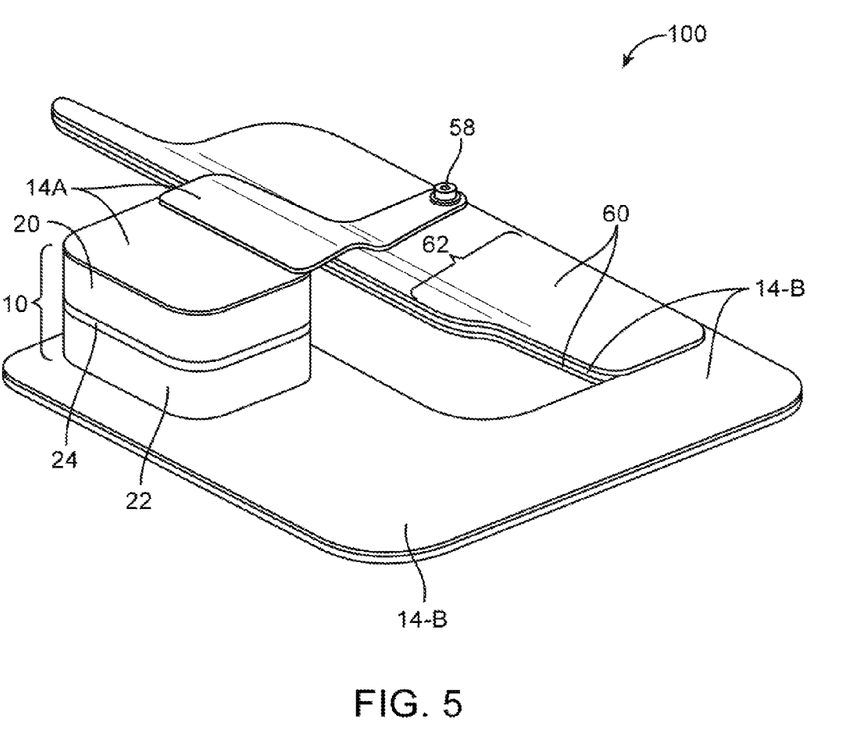
FIG. 5 is a diagram of an illustrative test system for gathering test data from device structures with a signal trace in accordance with an embodiment of the present invention.

FIG. 5 shows a perspective view of DSUTs 10 with test probe 14 positioned in contact with DSUTs 10 as shown in FIG. 4. Signal trace 14-A and ground trace 14-B may be made from metal sheets. Test probe 14 may lie in contact with substrates 20 and 22 during testing. As an example, signal trace 14-A may contact substrate 20 and ground trace 14-B may contact substrate 22. Signal trace 14-A and ground trace 14-B may be connected at a coaxial terminal 58, which may be a metal screw.

Signal trace 14-A may have a portion that slopes downwards to contact coaxial terminal 58. The portion of signal trace 14-A that contacts substrate 20 may have the surface area of the portion of substrate 20 that it is contacting. Signal trace 14-A may be formed such that the surface area of the portion of signal trace 14-A that slopes downward along slope 62 is gradually reduced until it makes contact with coaxial terminal 58. In other words, signal trace 14-A may be shaped such that the portion of signal trace 14-A contacting substrate 20 has a greater surface area than other portions of signal trace 14-A.

Coaxial terminal 58 may be at the same height level as ground trace 14-B. Ground trace 14-B may contact the entire bottom surface of substrate 22. A portion of ground trace 14-B may lie parallel to the sloping portion of signal trace 14A. An insulating material such as insulating material 60 may cover top and bottom surfaces of the sloping portion of ground trace 14-B such that insulating material 60 is interposed between signal trace 14-A and ground trace 14-B along slope 62. In other words, the only distance separating contact between signal and ground traces 14-A and 14-B along slope 62 may be the thickness of insulating material 60. The minimal distance between the signal and ground traces as well as the insulation provided by insulating material 60 may minimize loss of signal conducted through the metal traces from and to a test unit such as test unit 18 of FIG. 1.

Figure 6A:
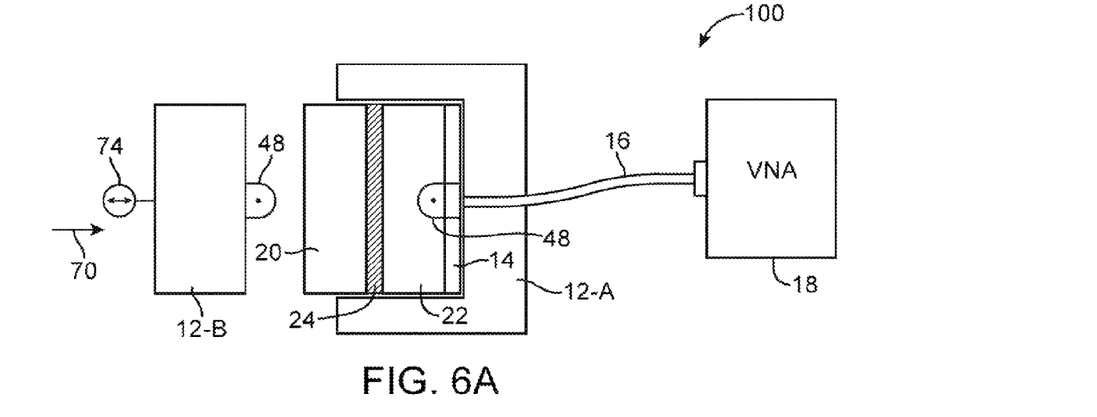
FIGS. 6A, 6B, and 6C are diagrams of a test system for exerting different types of forces on device structures under test in accordance with an embodiment of the present invention.
Figure 6B:
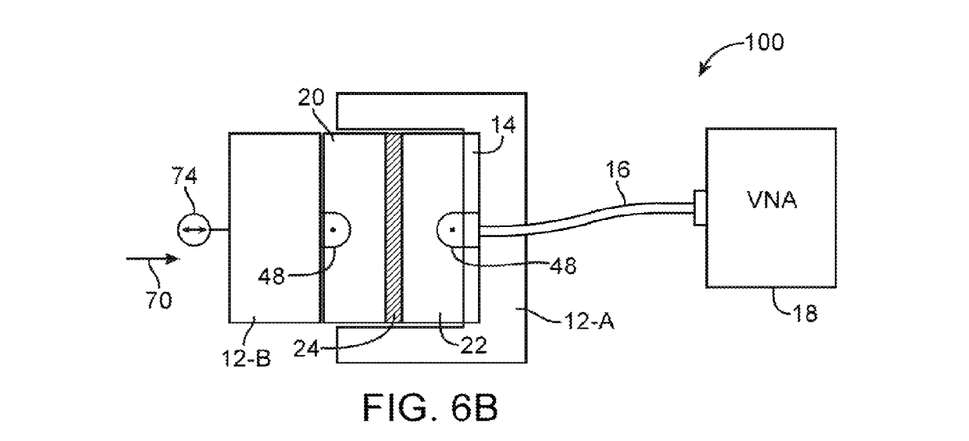
Figure 6C:
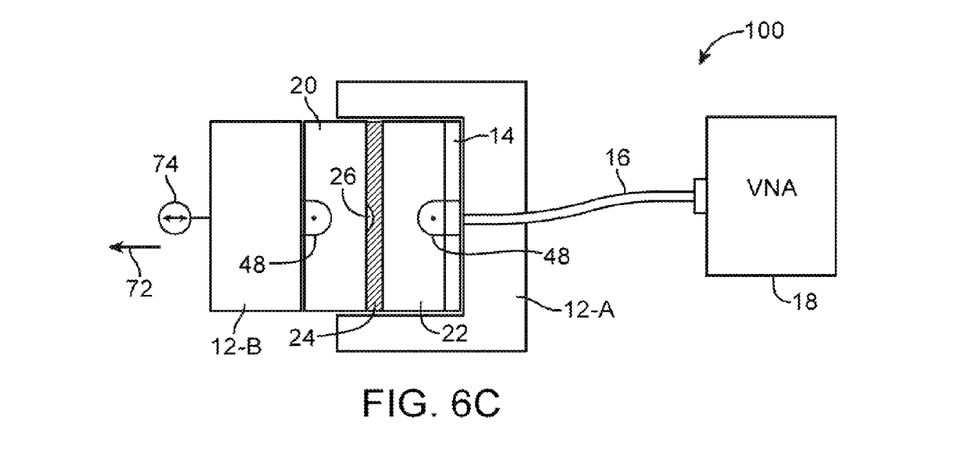

In FIGS. 6A-6C, DSUTs 10 may be tested using a test system 100 that applies pressure in a horizontal direction to DSUTs 10 rather than a vertical direction as shown in FIGS. 4A-4C. DSUTs 10 may be a stack under test as shown in FIG. 2 or other structures under test. DSUTs 10 may have substrates 20 and 22 and conductive material 24 interposed between the substrates. The test system may have VNA 18 connected to test probe 14 via a radio-frequency cable 16. Test probe 14 may have a signal contact and a ground contact that make electrical connections with DSUTs 10. Test probe 14 may gather test data about RF performance during testing from DSUTs 10 and send the test data to the vector network analyzer through cable 16.

Test fixture 12 may have portion 12-A that holds the substrate 22. Test fixture 12 may have portion 12-B that may be configured to apply pressure to DSUTs 10. In FIG. 6A, at the beginning of testing, test fixture portion 12-B may be in an initial position that is separated by a distance from DSUTs 10. Test fixture portion 12-B may be moved in direction 70 using positioner 74. Clamps 48 may be on test fixture portions 12-A and 12-B to secure DSUTs 10 to the test fixture.

During testing, test fixture portion 12-B may be moved using positioner 74 in direction 70 until it contacts substrate 20 of DSUTs 10, as shown in FIG. 6B. Test fixture portion 12-B may be attached to substrate 20 using an attaching structure such as clamp 48. Clamp 48 or other attaching structures may secure substrate 20 to test fixture 12-B. Test fixture 12-B may continue to move in direction 70 even after it has contacted test probe 14 to compress DSUTs 10.

Conductive material 24 may be a pressure-sensitive adhesive and compression of device structures 10 may activate conductive material 24. Activating conductive material 24 may allow substrate 20 and substrate 22 of the device structures to be securely bonded to each other so that DSUTs 10 may maintain conductivity through substrates 20 and 22 in stressed environments. Test fixture 12-B may continue moving in direction 70 after activation of conductive material 24 to administer more compressive stress on DSUTs 10 as illustrated by line 2 of FIG. 3A. Alternatively, test fixture 12-B may move in a direction opposite to direction 70 to reduce compressive stress on DSUTs 10 to an equilibrium point before applying more compressive stress to DSUTs 10 as illustrated by line 3 of FIG. 3A.

Compressive stress may cause deterioration of conductive material 24. The integrity of conductive material 24 may affect the conductivity of DSUTs 10 and consequently affect S11 scattering parameter test data collected from DSUTs 10 via cable 16. Deterioration of conductive material 24 may cause S11 parameter test data of DSUTs 10 to deviate from desired performance data.

However, if conductive material 24 is formed from a material resilient to compressive stress, DSUTs 10 may maintain conductivity under a particular level of compressive stress. For example, conductive material 24 may not deteriorate when DSUTs 10 experience a predetermined level of compressive stress 33b administered during testing. This may result in desirable S11 parameter test data and/or other satisfactory RF performance criteria and allow DSUTs 10 to pass on to subsequent testing or be used in a product device.

Test fixture 12-B may stop moving in direction 70 toward the device structures once conductive material 24 is activated and test fixture 12-B is securely fastened to substrate 20 with an attachment structure such as clamp 48. After compression of DSUTs 10, test fixture 12-B may then begin to move in a direction away from the DSUTs 10 such as direction 72 using positioner 74, as shown in FIG. 4C. Because substrate 20 is connected to test fixture portion 12-B and bottom substrate 22 is connected to test fixture portion 12-A, DSUTs 10 may experience tensile stress. Conductive material 24 may be stretched as substrate 20 is slowly pulled away from substrate 22.

Tensile stress may cause breaks or tears in conductive material 24 such as tear 26 as shown in FIG. 6C. The integrity of conductive material 24 may affect the conductivity of DSUTs 10 and consequently affect S11 parameter test data collected from DSUTs 10 via cable 16. Tear 26 may cause S11 parameter test data of DSUTs 10 to deviate from desired performance data.

However, if conductive material 24 is formed from a material resilient to tensile stress, DSUTs 10 may maintain conductivity under a particular level of tensile stress. For example, conductive material 24 may not deteriorate and create tear 26 when DSUTs 10 experience a predetermined level of tensile stress 33a administered during testing. This may result in desirable S11 parameter test data and/or other satisfactory RF performance criteria and allow DSUTs 10 to pass on to subsequent testing or be used in a product device.

Figure 7:
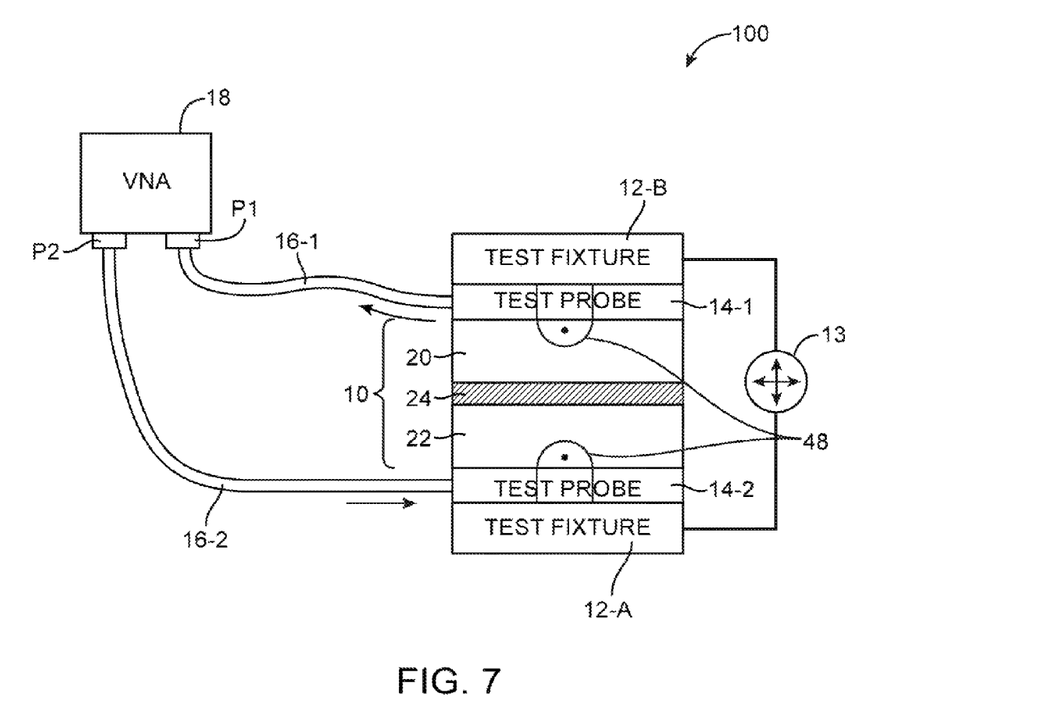
FIG. 7 is a diagram of an illustrative test system for characterizing device structures under test using multiple test probes in accordance with an embodiment of the present invention.

FIG. 7 shows a test system 100 for gathering multiport scattering parameter measurements from DSUTs 10 using two test probes such as test probe 14-1 and test probe 14-2 and VNA 18 with two test ports P1 and P2. Different types of test data such as different scattering parameter measurements (e.g., S11, S12, S21, and S22) may be gathered when each of the test probes 14 is used to transmit and receive test signals.

DSUTs 10 may include substrates 20 and 22 and conductive material 24 interposed between substrates 20 and 22. Conductive material 24 may be a pressure sensitive adhesive that bonds substrates 20 and 22 when activated by pressure. Test fixture 12 may hold the DSUTs 10. Portions of test fixture 12 may be moved using positioner 13. Test fixture portions 12-A and 12-B may both be connected as a part of an integral test fixture and may have clamps 48 that secure the test fixture to substrates 20 and 22 of DSUTs 10.

Test probe 14-1 may be positioned between substrate 20 and test fixture portion 12-B. Test probe 14-2 may be positioned between substrate 22 and test fixture portion 12-A. Each test probe 14 may have signal and ground conductors for transmitting and receiving RF test signals.

VNA 18 may be used to generate RF test signals that are transmitted to DSUTs 10. Port P1 may be connected to cable 16-1 and port 2 may be connected to cable 16-2. Cable 16-1 may have a first end that is connected to port P1 and a second end terminating at a first test probe 14-1. Similarly, cable 16-2 may have a first end that is connected to port P2 and a second end terminating at a second test probe 14-2.

As in FIGS. 1-6, RF test signals transmitted by VNA 18 and applied to DSUTs 10 through cable 16-1 and test probe 14-1 may energize DSUTs 10 and cause reflected signals to be sent back through the same cable 16-1. Test signals may also be sent to DSUTs 10 through cable 16-2 and test probe 14-2 and an energized DSUTs 10 may send reflected signals back through cable 16-2 to be received by VNA 18. These reflected signals may be used to compute a reflection coefficient (sometimes referred to as an S11 or S22 parameter).

When VNA 18 transmits RF test signals to DSUTs 10 through cable 16-1, corresponding emitted test signals may be received through cable 16-2. The transmitted signals sent through cable 16-1 and corresponding received signals from cable 16-2 may be used to compute a forward transfer coefficient (sometimes referred to as an S21 parameter). VNA 18 may also transmit RF test signals through cable 16-2 to DSUTs 10 and receive corresponding emitted test signals through cable 16-1 to compute an S12 parameter.

This is merely exemplary and does not limit the combinations of measurements that may be obtained; test system 100 may have any number of ports on test unit 18 and any number of RF cables and test probes. Test system 100 therefore may obtain any number of scattering parameter measurements that the number of ports, cables, and test probes allow.

Figure 8:
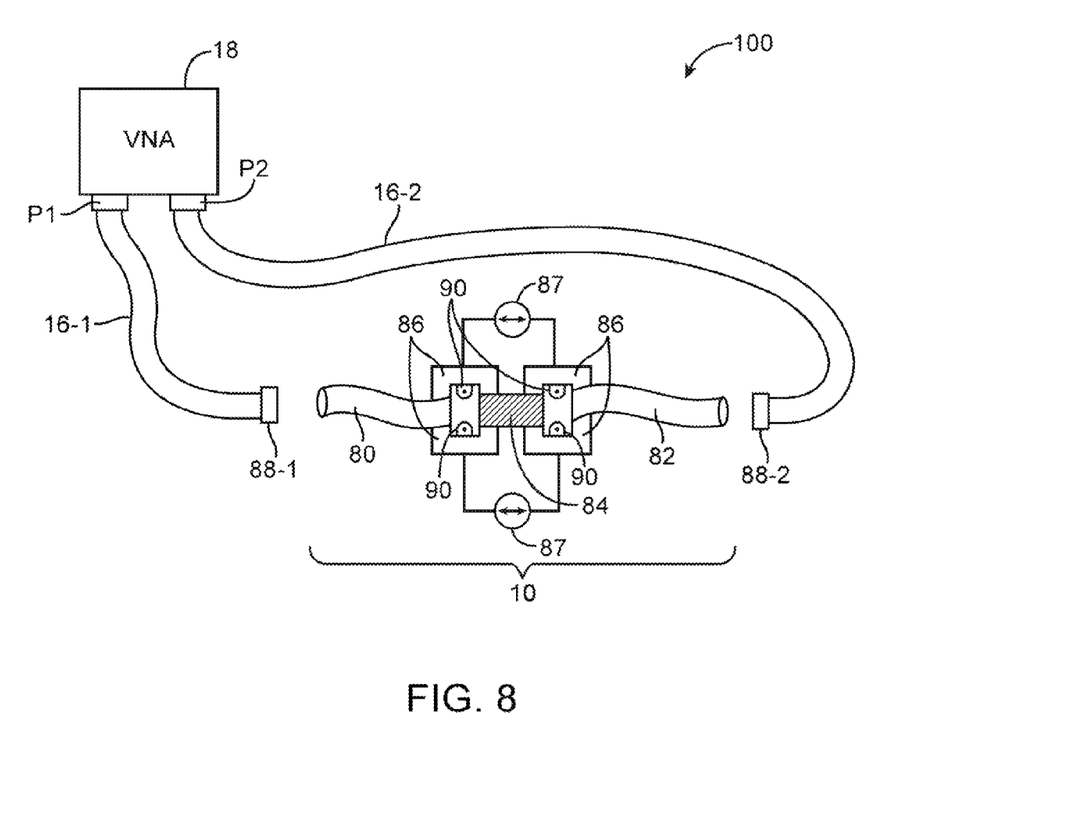
FIG. 8 is a diagram of an illustrative test system for characterizing device structures under test using coaxial cable connectors in accordance with an embodiment of the present invention.

FIG. 8 shows a test system 100 for testing DSUTs 10 including a coaxial cable with parts such as portions 80 and 82 joined by a conductive material such as conductive material 84. Conductive material 84 may be conductive adhesive, foam, tape, pressure sensitive adhesive, conductive gasket, conductive fabric foam, ultraviolet-activated adhesive, or thermal-activated adhesive. Coaxial cable portions 80 and 82 may be held by a test fixture such as test fixture 86. Portions of test fixture 86 may be moved using positioners 87 to apply pressure to DSUTs 10 in a way that compresses or stretches conductive material 84.

Conductive material 84 may be a pressure sensitive adhesive that may be activated by compressive pressure when test fixture 86 moves portions 80 and 82 toward each other. Tensile and/or compressive stress may be applied to coaxial cable portions 80 and 82 and conductive material 84 when test fixture 86 is moved using positioners 87 to pull portions 80 and 82 away from each other. Securing structures such as clamps 90 may be used to secure DSUTs 10 to testing fixture 86.

Coaxial cable portions 80 and 82 may be mated to RF cables such as cables 16-1 and 16-2 via radio-frequency coaxial test connectors 88-1 and 88-2. Cables 16-1 and 16-2 may be connected to ports P1 and P2 of VNA 18. VNA 18 may gather RF performance testing data from DSUTs 10. VNA 18 may transmit RF testing signals to DSUTs 10 via cables 16-1 and 16-2 and RF coaxial test connectors 88-1 and 88-2 to collect different measurements on RF performance (e.g., S11, S12, S21, S22).

VNA 18 may be used to generate RF test signals that are transmitted to DSUTs 10. Port P1 may be connected to cable 16-1 and port 2 may be connected to cable 16-2. Cable 16-1 may have a first end that is connected to port P1 and a second end terminating at a first RF coaxial test connector 88-1. Similarly, cable 16-2 may have a first end that is connected to port P2 and a second end terminating at a second RF coaxial test connector 88-2.

As in FIGS. 1-6, RF test signals transmitted by VNA 18 and applied to DSUTs 10 through cable 16-1 and RF coaxial test connector 88-1 may energize DSUTs 10 and cause reflected signals to be sent back through the same cable 16-1. Test signals may also be sent to DSUTs 10 through cable 16-2 and RF coaxial test connector 88-2 and the energized DSUTs 10 may send reflected signals back through cable 16-2 to be received by VNA 18. These reflected signals may be used to compute a reflection coefficient (sometimes referred to as an S11 or S22 parameter).

When VNA 18 transmits RF test signals to DSUTs 10 through cable 16-1, corresponding emitted test signals may be received through cable 16-2. The transmitted signals on cable 16-1 and corresponding received signals on cable 16-2 may be used to compute a forward transfer coefficient (sometimes referred to as an S21 parameter). VNA 18 may also transmit RF test signals through cable 16-2 to DSUTs 10 and receive corresponding emitted test signals through cable 16-1 to compute an S12 parameter.

Figure 9:
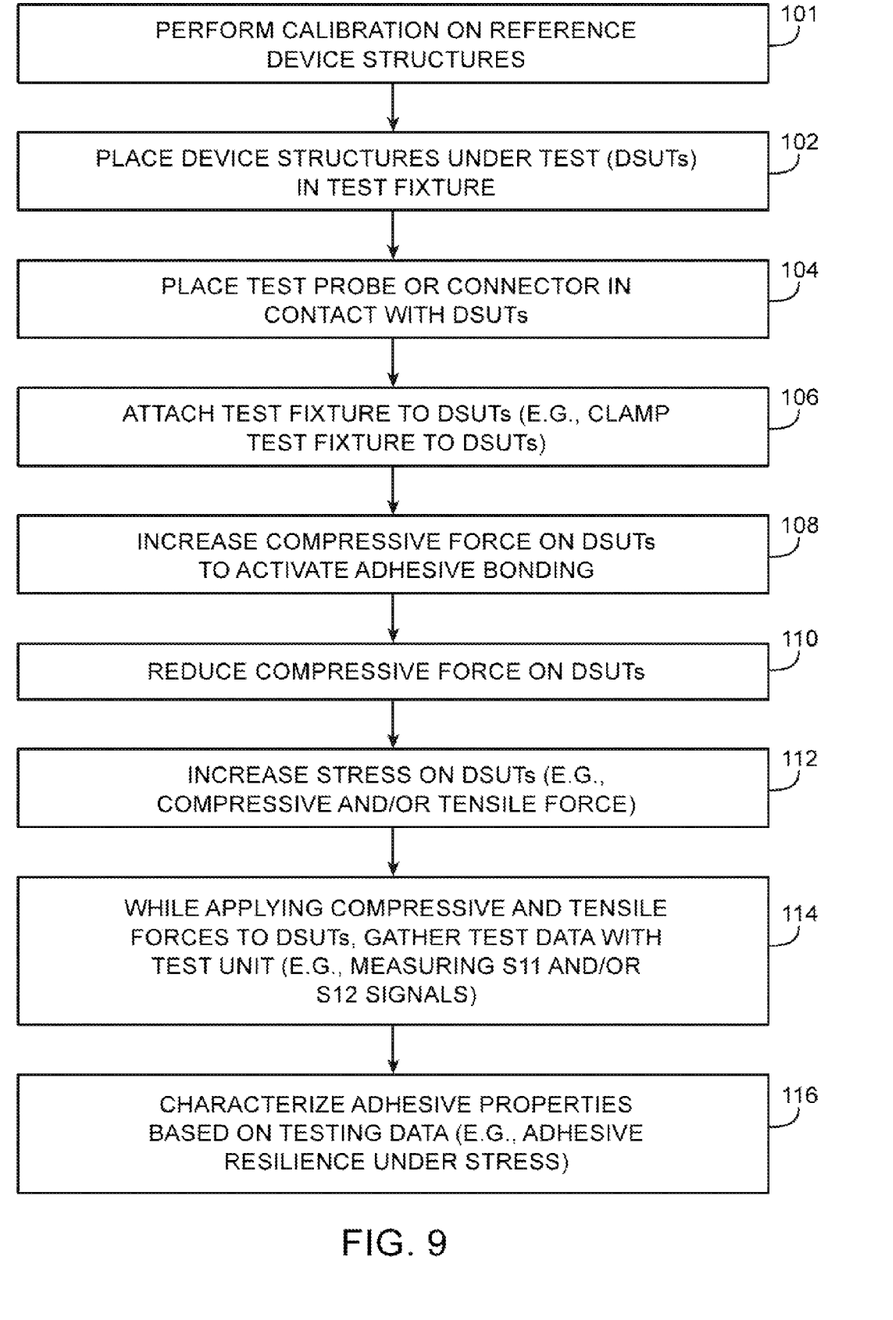
FIG. 9 is a flowchart of illustrative steps used to characterize device structures under test in a test system to evaluate radio-frequency performance of the device structures under test in accordance with an embodiment of the present invention.

FIG. 9 is a flowchart of illustrative steps used to evaluate radio-frequency characteristics of DSUTs 10 and to determine whether the radio-frequency characteristics of DSUTs 10 meet performance criteria. At step 101, calibration operations are performed on reference device structures. These reference device structures are structures that meet desired RF performance and design criteria. The test calibration data may provide a control reference point (i.e. an optimal S11 or S21 measurement) for comparison with gathered test data from DSUTs 10.

At step 102, device structures such as DSUTs 10 may be placed in a test fixture. DSUTs 10 may be a stacked structure of substrates such as substrates 20 and 22 joined by a layer of conductive material such as conductive material 24 as shown in FIG. 2, or a coaxial cable with portions such as coaxial cable portions 80 and 82 joined by a layer of conductive material such as conductive material 84 as shown in FIG. 8. Test fixtures used to test the device structures under test may be any of the test fixtures described in FIGS. 1-8, such as test fixture 12 and test fixture 86.

At step 104, a test probe such as test probe 14 or a connector such as RF coaxial test connector 88 may be placed in contact with the device structures under test. Test probe 14 may have a signal and a ground trace that is positioned in contact with device structures under test as shown in FIG. 5. There may be any number of test probes and connectors at any number of locations electrically connected to device structures under test in a way that allows signals to be successfully transmitted and received between DSUTs 10 and test unit 18.

At step 106, a test fixture such as test fixture 12 or test fixture 86 may be attached to DSUTs 10. The test fixture may be attached to DSUTs 10 using clamps such as clamps 48 or 90. The clamps may secure DSUTs 10 to the fixture such that when parts of the test fixture are moved during testing, DSUTs 10 stay attached to the test fixture.

At step 108, a compressive force may be increased on DSUTs 10 to activate adhesive bonding as shown in FIGS. 4B and 6B. DSUTs 10 may have a conductive material that may be a pressure sensitive adhesive. The pressure sensitive adhesive may be activated by compressive force to bond portions of the device structures that are in contact with the adhesive such as substrates 20 and 22 as shown in FIG. 2.

At step 110, once the adhesive is activated and substrates 20 and 22 are securely bonded in the device structures under test, compressive force on the device structures may be reduced. For example, as shown in FIG. 4B, test fixture portion 12-B may stop moving in a downward direction and instead begin to move in an upward direction. Step 110 may be optional when testing DSUTs under compressive stress (e.g., using the force loading profile as illustrated by line 2 of FIG. 3A).

At step 112, an increased stress (e.g. compressive and/or tensile force) may be applied to a portion of DSUTs 10. For example, as shown in FIGS. 4C and 6C, test fixture portion 12-B may be moved in a direction away from test fixture portion 12-A and consequently "stretch" the conductive material (e.g. adhesive) bonding two substrates in the device structures under test.

At step 114, while applying compressive and tensile forces to the device structures, test data may be gathered with the test unit. Scattering parameter measurements (e.g., S11, S12, S21, S22) and additional RF measurements may be collected, depending on the number of ports on the test unit and the number of test probes and/or coaxial cables used, as shown in FIGS. 4A-C, 6A-C, 7, and 8.

At step 116, properties of the adhesive or other conductive material in DSUTs 10 are characterized based on the testing data. In other words, scattering parameter measurements or other measurements gathered by the test unit may be used to determine whether the resilience of the adhesive or the conductive material in DSUTs 10 is satisfactory according to desired industry standards.

The foregoing is merely illustrative of the principles of this invention and various modifications can be made by those skilled in the art without departing from the scope and spirit of the invention. The foregoing embodiments may be implemented individually or in any combination.

What is claimed is:

1. A method for using a test system to characterize device structures under test, where the test system includes a test unit and a test fixture, the method comprising:
    activating pressure-sensitive adhesive material in the device structures under test by applying pressure to the adhesive material;
    once the pressure-sensitive adhesive material has been activated, applying stress to the device structures under test with the test fixture; and
    while the stress is applied to the device structures under test, gathering test data on the device structures under test with the test unit, wherein the gathered test data comprises radio-frequency scattering parameter measurements.

2. The method defined in claim 1, wherein applying the stress to the device structures under test further comprises applying compressive stress to the device structures under test and applying tensile stress to the device structures under test.

3. The method defined in claim 1, wherein applying the stress to the device structures under test comprises applying different amounts of stress to the device structures under test.

4. A method for using a test system to characterize device structures under test, wherein the test system includes a test unit and a test fixture and wherein the device structures under test include an adhesive material, the method comprising:
    with the test fixture, applying tensile stress to the device structures under test;
    while the tensile stress is applied to the device structures under test, gathering radio-frequency scattering parameter measurements on the device structures under test with the test unit; and
    with the test unit, determining whether the adhesive material exhibits any defects by analyzing the gathered radio-frequency scattering parameter measurements.

5. The method defined in claim 4, further comprising:
    applying compressive stress to the device structures under test with the test fixture.

6. The method defined in claim 4, wherein the adhesive material is conductive, the method further comprising:
    analyzing the gathered radio-frequency scattering parameter measurements to determine whether the adhesive material satisfies design criteria.

7. The method defined in claim 4, wherein gathering the radio-frequency scattering parameter measurements comprises gathering reflection coefficient measurements on the device structures under test.

8. The method defined in claim 4, wherein gathering the radio-frequency scattering parameter measurements comprises gathering multiport scattering parameter measurements on the device structures under test.

9. The method defined in claim 4, wherein applying the tensile stress comprises increasing the applied tensile stress at regular increments.

10. A test system, comprising:
    a test fixture that is configured to receive device structures under test and that is configured to apply tensile stress on device structures under test while the device structures under test are received within the test fixture;
    a test unit configured to gather test data on the device structures under test; and
    a test probe that receives radio-frequency test signals from the test unit and that is coupled to the device structures under test.

11. The test system defined in claim 10, wherein the test fixture is further configured to activate an adhesive material in the device structures under test while the device structures under test are received within the test fixture.

12. The test system defined in claim 10, wherein the test probe comprises a signal conductor and a ground conductor, and wherein the device structures under test are interposed between the signal conductor and the ground conductor while the device structures under test are received within the test fixture.

13. The test system defined in claim 10, further comprising:
    a radio-frequency cable having a first end that is coupled to the test unit and a second end that is mated to a corresponding coaxial cable in the device structures under test via a radio-frequency coaxial test connector.

14. The test system defined in claim 10, wherein the test unit comprises a radio-frequency tester operable to gather scattering parameter measurements on the device structures under test.

* * * * *